United States Patent [19]

Gibbons et al.

[11] Patent Number: 4,868,129

[45] Date of Patent: Sep. 19, 1989

[54] APPARATUS AND METHOD FOR DILUTION AND MIXING OF LIQUID SAMPLES

[75] Inventors: Ian Gibbons, Menlo Park; Robert S. Hillman, Cupertino; Channing R. Robertson, Stanford, all of Calif.

[73] Assignee: Biotrack Inc., Mountain View, Calif.

[21] Appl. No.: 90,026

[22] Filed: Aug. 27, 1987

[51] Int. Cl.$^4$ .......................... G01N 1/10; B01L 3/02
[52] U.S. Cl. .................................. 436/179; 436/180; 422/100
[58] Field of Search ................. 422/99, 100, 296–299, 422/102; 436/179, 180, 176; 73/864.02, 864.12, 864.52; 141/4, 7, 9, 285

[56] References Cited

U.S. PATENT DOCUMENTS

| | | | |
|---|---|---|---|
| 3,182,865 | 5/1965 | Anscherlik | 422/100 |
| 3,186,808 | 6/1965 | Anscherlik | 422/100 |
| 3,607,100 | 9/1971 | Croom | 422/100 |
| 4,473,457 | 9/1984 | Columbus | 422/100 |
| 4,503,012 | 3/1985 | Starr | 422/100 |
| 4,504,404 | 3/1985 | Englander | 422/100 |
| 4,596,780 | 6/1986 | Castaneda | 436/179 |
| 4,610,170 | 9/1986 | Ekholm et al. | 436/179 |

FOREIGN PATENT DOCUMENTS 3328964 2/1985 Fed. Rep. of Germany.

Primary Examiner—Barry S. Richman
Assistant Examiner—T. J. Wallen
Attorney, Agent, or Firm—Richard L. Neeley

[57] ABSTRACT

An apparatus for diluting a sample with a diluent, comprising a fixed volume measuring chamber, a fixed volume receiving chamber and fluid receiving relationship to the measuring chamber, a gas vent in the receiving chamber, a stop flow junction between the measuring chamber and the receiving chamber, a sample application site in fluid donating relationship to the measuring chamber, wherein the vertical height difference between the sample application site and the stop flow junction is insufficient to provide a hydrostatic pressure capable of overcoming backpressure at the stop flow junction when sample is applied to the sample application site, and the diluent application site and fluid donating relationship to the measuring chamber. Sample and diluent are added sequentially to the apparatus of the invention without requiring any intervening operations. Various means are provided for restarting flow, which causes diluent to wash the sample into the receiving chamber, where the two can be mixed.

27 Claims, 3 Drawing Sheets

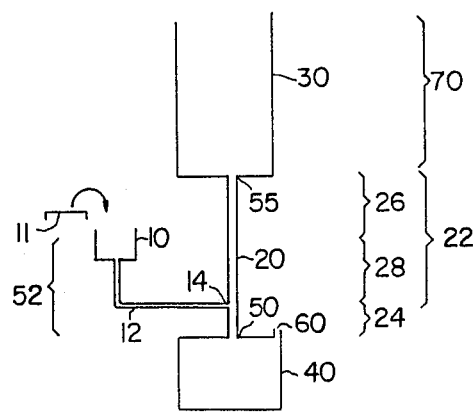
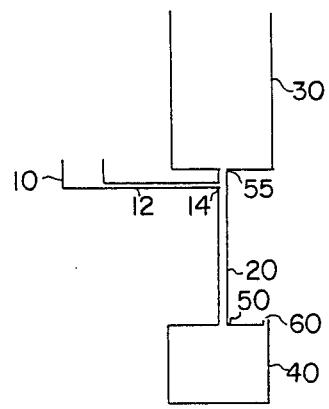
FIG.1　　　　　FIG.2
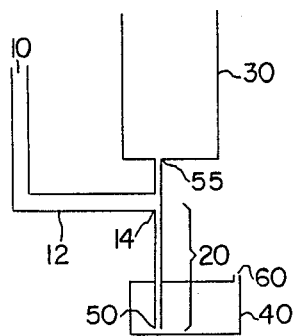
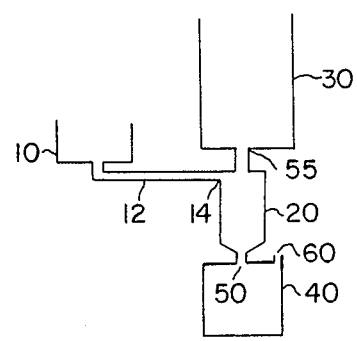
FIG.3　　　　　FIG.4
FIG.5　　　　　FIG.6
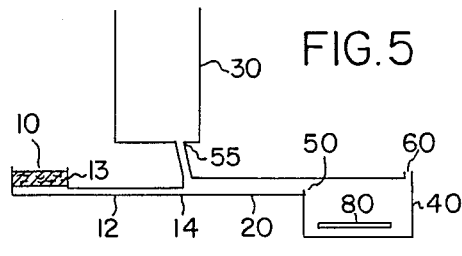
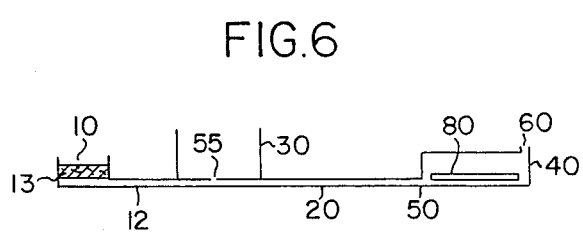

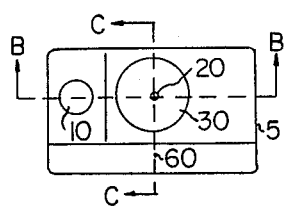
FIG.13A
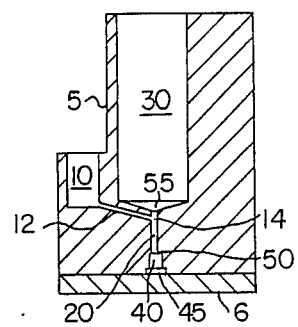
FIG.13B
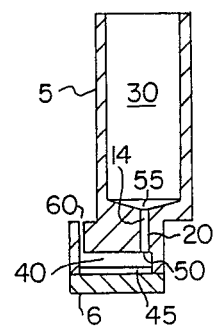
FIG.13C
FIG.14A
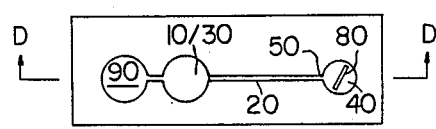
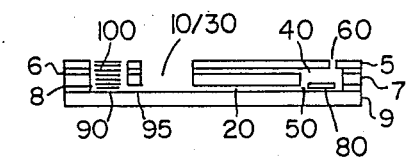
FIG.14B
FIG.15A
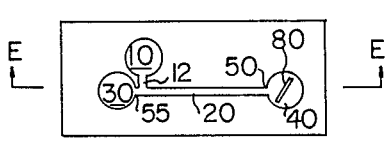
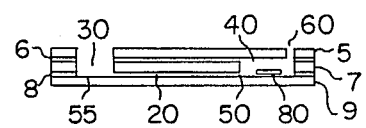
FIG.15B
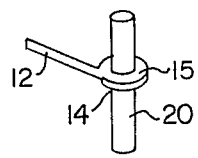
FIG.16A
FIG.16B

APPARATUS AND METHOD FOR DILUTION AND MIXING OF LIQUID SAMPLES

INTRODUCTION

1. Technical Field

This invention relates to methods and apparatuses used for diluting and mixing liquids, particularly the automatic measuring and diluting of small volumes of liquids.

2. Background

There has been a recent period of explosive growth in the field of clinical analyses intended to be carried out by unskilled users. Numerous approaches have been developed which allow an unskilled user, such as a diabetic patient, to determine the presence and/or amount of an analyte in a sample, such as glucose in urine. The devices that carry out such analyses are generally intended to be "user friendly" in that they require little training and are essentially fool-proof in use. Typical of these devices are the so-called "dipsticks". These devices are plastic strips with a reagent-containing matrix layered thereon. Sample is applied to the strip, and the presence or absence of an analyte is indicated by a color-forming reaction While such devices have proven useful for the qualitative determination of numerous substances in biological samples, not all analyses can be carried out in this manner. For example, some techniques require dilution and/or mixing of small quantities of sample. Measurement of extremely small amounts (e.g., microliter amounts) of liquid and the dilution thereof typically require significant training or the use of expensive equipment to carry out the dilution. Neither of these alternatives is user-friendly.

Measuring and dilution of small samples of liquid is readily carried out in a number of automatic analyzers. However, these are not suitable for use in the home or in a doctor's office because of their size and expense. For example many devices are available in which a sample of liquid is drawn into a conduit which is in the form of a capillary tube that acts as a metering device. However, this metering device is part of a large apparatus containing pistons and numerous other moving parts, such as vacuum pumps, that are required for movement of the sample and diluent. The precision with which such moving parts must be manufactured in order to retain liquid-tight seals significantly increase the cost of the device.

As an alternative to large automatic analyzers, small hand-held micropipets, such as the well known Eppendorf ® pipet, have been devised. These pipets utilize a precision piston to draw sample or diluent into a small disposable tip. However, skill is required in the use of the pipet, and a number of hand operations must be carried out to successfully measure sample and diluent. Skill is also required in mixing the resulting small-volume solution.

Another technique that has been developed for the home uses a capillary tube to measure a sample of fluid. The entire capillary tube is then placed into a large container which holds a premeasured quantity of diluent or to which a measured quantity of diluent is added. However, such devices are not generally satisfactory in the hands of an unskilled user, since capillary tubes are easily broken and since contamination of the outside of the capillary results in volume error.

Accordingly, there is a need for a simple and accurate methods and devices for measuring, diluting, mixing, and analyzing small quantities of sample.

Relevant Literature

West German published patent application No. DE3328964C1, publication date Feb. 14, 1985, describes a device for the automatic, discontinuous sampling of fluids using a capillary tube that acts as a measuring device and which can be either dipped into a fluid being sampled or alternatively moved into a position from which the sample is transported with a diluent to an analyzer by a pump or suction. U.S. Pat. No. 4,454,235 describes a capillary tube holder for liquid transfer in immunoassays. U.S. Pat. No. 4,233,029 describes a liquid transport device formed by opposed surfaces spaced apart a distance effective to provide capillary flow of liquid without providing any means to control the rate of capillary flow. U.S. Pat. Nos. 4,618,476 and 4,233,029 describe a similar capillary transport device having speed and meniscus control means. U.S. Pat. No. 4,426,451 describes another similar capillary transport device including means for stopping flow between two zones, flow being resumed by the application of an externally-generated pressure. U.S. Pat. Nos. 3,811,326; 3,992,150; 4,537,747; and 4,596,780 describe various processes and devices in which a capillary tube is used to take up a predetermined volume of the test solution and the charged capillary is in place in a cuvette or other container of liquid that is used as reagent or diluent. U.S. Pat. No. 3,799,742 describes an apparatus in which a change in surface character from hydrophilic to hydrophobic is used to stop flow of a small sample, thereby metering the sample present.

SUMMARY OF THE INVENTION

The present invention provides a self-contained dilution apparatus that does not require the use of external force (except unassisted gravity in some cases) to move liquids between its various parts and provide for reproducible dilution of samples. The apparatus comprises a fixed volume measuring chamber; a fixed volume receiving chamber in fluid receiving relationship to the measuring chamber: a gas vent in the receiving chamber: a stop flow junction between the measuring chamber and the receiving chamber; a sample application site in fluid donating relationship to the measuring chamber, wherein the vertical height difference between the sample application site and the stop flow junction is insufficient to provide flow through the stop flow junction when sample is applied to the sample site: and a diluent application site in fluid donating relationship to the measuring chamber. Means for starting flow at the stop flow junction are provided in some cases internally in the apparatus and in other cases are provided by external forces and/or devices. The stop flow junction uses backpressure caused by surface tension to stop flow of liquid under some circumstances while allowing flow under others The stop flow junction acts as a valve but has no moving parts, relying on surface tension and the geometry of the junction to accomplish its function. Various means for starting flow include locating the diluent application site sufficiently above the stop flow junction to provide enough hydrostatic pressure to overcome the backpressure at the stop flow junction, including a movable arm or other device proximate to the stop flow junction in order to break surface tension, or providing a vibrator (optionally located externally to the apparatus) to break surface tension. In all cases in which external force is applied as a means for starting flow, this external force is not required for continued flow once flow resumes.

In operation, the apparatus is used in a method in which a sample is applied to the sample application site, whereby the liquid sample flows by capillary action or under the influence of gravity into the fixed volume measuring chamber. Flow stops when the sample reaches the stop flow junction. Diluent is then added to the diluent application site. Any necessary external force required to activate the means for starting flow is then applied, if necessary, so that diluent displaces the sample from the fixed volume measuring chamber into the fixed volume receiving chamber. The geometry of the measuring chamber is such that diluent displaces the sample rather than flowing through the sample without displacing it. Once the backpressure of the stop flow junction is overcome, no external force (other than gravity in some cases) is required for this liquid movement. A gas vent is provided in the receiving chamber in order to allow gas to escape and liquid to flow into the receiving chamber. Diluent continues to flow until the fixed volume receiving chamber is completely filled with a known mixture of sample and diluent.

Optional means for mixing can be provided in the receiving chamber. The means for mixing and means for starting flow can be different or the same (for example, a stirring bar can be used both to break surface tension at the stop flow junction and to mix the sample and diluent in the receiving chamber). In various embodiments of the invention, the receiving chamber or other parts of the apparatus can contain reagents and the receiving chamber can be utilized to provide a suitable location for an optical or other type of measurement. In other embodiments, means can be provided for removing sample from the receiving chamber for further operations at other locations.

BRIEF DESCRIPTION OF THE DRAWINGS

The present invention will be better understood by reference to the following detailed description of the invention when considered in conjunction with the attached drawings that form a part of the present specification, wherein:

FIG. 1 is a vertical cross-section showing the internal liquid-contacting surfaces of a first embodiment of the invention.

FIG. 2 is a vertical cross-section showing the internal liquid-contacting surfaces of a second embodiment of the invention.

FIG. 3 is a vertical cross-section showing the internal liquid-contacting surfaces of a third embodiment of the invention.

FIG. 4 is a vertical cross-section showing the internal liquid-contacting surfaces of a fourth embodiment of the invention.

FIG. 5 is a vertical cross-section showing the internal liquid-contacting surfaces of a fifth embodiment of the invention.

FIG. 6 is a vertical cross-section showing the internal liquid-contacting surfaces of a sixth embodiment of the invention.

FIG. 13A provides a plan view and FIGS. 13B and 13C provide vertical cross-sectional views of a thirteenth embodiment of the invention.

FIG. 14A provides a plan view and FIG. 14B provides a vertical cross-sectional view of a fourteenth embodiment of the invention.

FIG. 15A provides a plan view and FIG. 15B provides a vertical cross-sectional view of a fifteenth embodiment of the invention.

FIG. 16A is a perspective view and FIG. 16B is a vertical cross-sectional view of a junction corresponding to junction 14 of FIG. 13B modified to have a capillary channel to encourage flow of a sample from a capillary channel into a larger chamber.

DESCRIPTION OF SPECIFIC EMBODIMENTS

Figure 7:
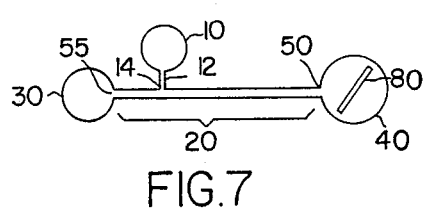
FIG. 7 is a horizontal cross-section showing the internal liquid-contacting surfaces of a seventh embodiment of the invention

The present invention provides an apparatus and a method by which small samples can easily be measured and diluted. The apparatus is small, convenient to use, and requires no moving parts for the movement of fluid, although moving parts are provided in some embodiments to initiate the movement of fluid after fluid flow has been stopped at a stop flow junction. Accordingly, the apparatus is easy to use, inexpensive to manufacture and can be used in a large number of procedures in which dilution of a small sample is required.

The parts of the apparatus include a fixed volume measuring chamber, a fixed volume receiving chamber in fluid receiving relationship to the measuring chamber, a vent to allow gas (e.g., air) to leave the receiving chamber, a stop flow junction between (preferably at the intersection of) the measuring chamber and the receiving chamber, a sample application site, and a diluent application site. Means for starting flow at the stop flow junction are provided in some embodiments. When a sample is present in the fixed volume measuring chamber but no diluent is present, the sample is prevented from flowing into the receiving chamber by backpressure created by surface tension at the stop flow junction.

The various parts and the function of the various parts can be understood by following the course of action as a sample is applied to the apparatus and is diluted. The following description follows this plan of organization.

The sample is a liquid and may be derived from any source, such as a physiological fluid; e.g., blood, saliva, occular lens fluid, cerebral spinal fluid, pus, sweat, exudate, urine, milk, or the like. The liquid sample may be subjected to prior treatment, such as preparing serum or plasma from blood or dissolving or suspending a solid in a liquid. Examples of sample treatments prior to application to the apparatus of the invention include concentration, filtration, distillation, dialysis, inactivation of natural components, chromatography, and addition of reagents. In addition to physiological fluids, other liquid samples can be employed. Examples of other liquid samples include process streams, water, plant fluids, chemical reaction media, biological growth media, and the like. For the most part, the liquid will be aqueous, although other liquids can be employed. Aqueous media may contain additional miscible liquids, particularly oxygenated organic solvents, such as lower alkanols, dimethyl formamide, dimethyl sulfoxide, acetone, and the like. Usually the solvents will be present in less than about 40 vol %, more usually in less than about 20 vol %, in order to maintain the high surface tension that is present in aqueous solutions. However, the apparatus of the invention can be modified as described below for use with liquids exhibiting different surface tensions The sample application site will generally be a cavity on a surface of the apparatus or may simply be an opening (optionally surrounded by a ring or tube) leading to the interior of the apparatus. The sample application site can contain a filter, for example, to separate red blood cells from plasma, or may represent a connection between the apparatus of the invention and some other apparatus that manipulates the sample prior to its entering the present dilution apparatus.

When sample is applied to the sample application site, the liquid sample flows without the application of external force (except unassisted gravity) into the fixed volume measuring chamber. A capillary channel or other channel capable of transporting fluid can connect the sample application site to the measuring chamber, or the capillary or other channel exiting the sample application site can itself be the measuring chamber. The measuring chamber ean be a capillary channel or chamber, in which case capillary action will aid or in some cases provide all the force necessary for filling the measuring chamber with sample from the sample application site. Capillary channels and chambers will generally have at least one dimension perpendicular to the flow path in the range 0.01 to 2.0 mm, more generally 0.1 to 1.0 mm. However, larger measuring chambers are also possible. The sample application site is said to be in "fluid donating relationship" to the measuring chamber in order to indicate that unassisted flow occurs. The geometry of the measuring chamber is such that when diluent is added to the apparatus at a later step, essentially all of the sample in the measuring chamber will be expelled into the receiving chamber. This is typically accomplished by providing for smooth flow of liquid through the measuring chamber. A straight tube open at both ends is thus a preferred embodiment. In preferred embodiments, diluent enters the measuring chamber in a front across the entire cross-sectional area of flow. This helps avoid mixing of diluent with sample and passage of diluent through the measuring chamber without expelling essentially all of the sample, which can occur if a small stream of diluent enters into a broader cross-sectional area of the measuring chamber When sample flows into the fixed volume measuring chamber, flow stops when sample reaches the stop flow junction, so called because it marks the junction between the early part of the fluid track in which sample flows freely and the later part of the fluid track into which sample does not normally flow until the user has had time to initiate the dilution process. Since the stop flow junction exists at the limit of the flow path of the sample, it will be found at one end of the measuring chamber In some cases, this same location will be the beginning of the receiving chamber (i.e., when the two chambers are directly connected). However, in other cases an additional channel may connect the stop flow junction to the receiving chamber It should be recognized that flow stop can occur both stably and metastably. A metastable flow stop is one in which flow stops on the macroscopic level but may resume without apparent cause after a time interval of a few seconds to a few minutes. Gradual creep of liquids along container walls or through microscopic or submicroscopic channels resulting from imperfections in the manufacturing process is believed to be the mechanism by which flow starts again once it has stopped. Additionally, small, undetectable vibrations (such as might be caused by persons walking near the apparatus or starting and stopping of nearby equipment, such as air-conditioning units) may also be sufficient to start flow in a metastable situation. However, there is no requirement of absolute stability since the apparatus is designed for addition of a diluent and eventual starting of flow at the stop flow junction. Accordingly, any flow stop which can be sustained for at least 10 seconds, preferably at least one minute, and more preferably at least five minutes, is sufficient for the purposes of this invention.

The stop flow junction is not a valve as it has no moving parts. Rather, this junction relies on backpressure from the surface tension of the liquid sample to stop flow. This backpressure can be created in a number of ways. For example, backpressure is created when the cross-sectional area of the flow path increases in a region in which there is contact between the liquid and the container walls (e.g., when a small tube enters a larger chamber or when the cross-sectional area of a channel increases). Greater backpressure and more consistent operation is achieved when the increase in cross-sectional area of the flow path is abrupt rather than gradual, particularly when there is a break in capillarity in the sample flow path. Imperfections in the container walls during gradual widening of chambers may cause liquid to "creep" more on one side than another, thereby avoiding the creation of backpressure. Liquid can also creep around corners when imperfections are present. Unbalanced forces will also be present when the junction is not horizontal. A horizontal junction, for example, occurs when a vertical tube enters the top horizontal surface of a chamber. If a horizontal tube enters a vertical wall of a container, a vertical junction is present, and the pressure at the bottom of the stop flow junction will be greater than the pressure at the top of the junction, due to hydrostatic pressure caused by the different heights of liquid. Nonetheless, non-horizontal stop flow junctions can be created by reducing the diameter of the smaller channel containing liquid as it enters the larger area, thereby reducing the difference in pressure between the upper and lower portions of the junction.

In many cases, the junction will be formed when a small-diameter measuring tube (i.e., measuring chamber) enters a larger receiving chamber. A small measuring chamber can enter the larger receiving chamber at a right angle or at an angle other than a right angle. The angle between the internal wall of the small tube and the surface of the chamber in the latter case will be different at different locations around the circumference of the junction.

U.S. Pat. No. 4,426,451, which is herein incorporated by reference, describes a number of stop flow junctions that it refers to as "meniscus control means" for use in a device in which there is capillary flow from one zone to another. The stop flow junctions described in that patent can be used in the apparatus of the present invention. However, the patent is not directed to stopping flow when the second zone is not a capillary zone. In contrast to the specific teachings of the patent, which indicate that the walls of the capillary chamber must gradually narrow and gradually expand in order to provide for flow stop, an abrupt widening has been found to be more effective in the practice of the present invention when the second chamber (here the receiving chamber) is not a capillary space. Although it is recognized that imperfections will exist on the molecular level, it is preferred that the junction be as sharp as possible from a macroscopic view point, approaching as closely as possible the ideal junction formed by the intersection of the plane (which can be curved) forming the walls of the measuring chamber with the plane forming the wall of the receiving chamber surface in which the stop flow junction is found. Maintaining a horizontal junction to avoid pressure differentials, reducing the area of the junction, changing the surface of the capillary so as to decrease the hydrophilic character (for aqueous solutions), providing smooth surfaces (rough surfaces encourage creep of liquid along the surface), and providing an abrupt change in cross-sectional area (preferably providing an angle between intersecting surfaces of about 90° or lower) all operate to prevent creep of liquid from one chamber to the other.

In general, for small (capillary size) junctions, the backpressure will be controlled by the smallest radius of curvature assumed by the meniscus. For example, when a capillary tube with a circular cross-section enters a larger space so that liquid bulges out into the space under hydrostatic pressure, the meniscus will be approximately spherical, and the backpressure ($\Delta p$) is given by the Young-Laplace equation: $\Delta p = 2\gamma/R$, where $\gamma$ is the surface tension of the sample fluid and R is the radius of curvature. See, Miller and Neogi, "Interfacial Phenomena: Equilibrium and Dynamic Effects", Marcel Dekker, Inc., New York, 1985, and Davies and Riedeal "Interfacial Phenomena", 2nd Ed., Academic Press, New York, 1963. If the fluid meets the surface at an angle greater than 0°, this backpressure will be reduced by a geometric term. The radius, R, will change (become smaller) as the hydrostatic pressure increases, so that the backpressure and hydrostatic pressure balance. As hydrostatic pressure increases, R reaches a minimum value (maximum curvature) determined by the geometry of the device and the contact angle. The corresponding backpressure defines the maximum hydrostatic pressure sustainable by the stop flow junction.

On the other hand, junctions between other chambers and capillaries through which flow is intended to be continuous can be specifically designed to encourage rather than discourage flow. In order to encourage flow, the opposite approach is taken from that indicated above for stopping flow (e.g., increasing rather than reducing the area of the junction or providing a gradual change in cross-sectional area). In a preferred example of such flow junctions, a capillary groove extending in the direction of fluid flow can encourage flow past a junction. An example of such a groove is provided later in a specific embodiment.

Backpressure is also created when the surface that the liquid contacts changes to decrease adhesion between the liquid and the container wall (for example, when an aqueous sample moves from a hydrophilic to a hydrophobic surface). The surface properties of the various interior surfaces of the device of the invention can and generally will be controlled by various physical and/or chemical treatments. For a discussion of controlling surface properties of similar devices, see commonly assigned U.S. patent application Ser. No. 880,793, filed July 1, 1986. For example, plastic surfaces can be treated to increase their hydrophilicity. Either the whole apparatus or specific parts can be treated. Alternatively, different parts of the apparatus can be made of different plastics. For capillary flow, contact angles of 0°–90° are sufficient, preferably 1085° and most preferably 30°–70°. In order to provide these contact angles for aqueous samples, the capillary surfaces will be hydrophilic. For non-aqueous liquids, a hydrophobic surface would be appropriate. By using a combination of container wall geometry and surface wetability, a backpressure range of from 0 (no change in cross-sectional area or surface adhesion) to 20 cm $H_2O$ and higher can be achieved with water as the liquid. When the backpressure is 0, the location in question is not a stop flow junction. A stop flow junction occurs when there is sufficient backpressure to prevent the flow of sample past a particular point in the flow path; e.g., from the fixed volume measuring chamber to the fixed volume receiving chamber.

When the sample flow stops at the stop flow junction, the measuring chamber contains a fixed volume of sample. When diluent is added to the diluent application site and flow is restarted (see discussion below), diluent displaces the fixed volume of the sample into the receiving chamber and continues to flow into the receiving chamber in order to dilute the sample. The portion of the interior chambers that is displaced into the receiving chamber defines the measured, fixed volume. The fraction of the internal spaces of the apparatus that actually form the measuring chamber will depend upon the geometry of the apparatus but will be readily apparent from operation of the device.

Two ways by which flow can be started are to decrease the backpressure due to surface tension or to increase the hydrostatic pressure at the stop flow junction. In preferred embodiments of the invention, flow is started automatically when diluent is added by locating the diluent application site at a height sufficiently above the stop flow junction to provide increased forward hydrostatic pressure that is capable of overcoming the backpressure caused by surface tension. Use of gravity-created hydrostatic pressure allows sequential addition of sample and diluent (without requiring the use of external force on the apparatus) to both measure sample and measure and initially mix the diluent. Forward hydrostatic pressure can also be increased by re-orienting the device so the vertical height of the liquid column over the junction increases. Complete mixing of sample and diluent, if needed or desired, can be accomplished later in such devices by a magnetic stir bar or other means as described below.

Motion of the apparatus can also be used to start fluid flow. A single, sharp, short start/stop movement or a vibrating motion are both suitable. Neither a single sharp motion nor a vibration is itself capable of causing sustained fluid flow, since the starting and stopping motions cause forces to be exerted in opposite directions, and therefore would cause no net motion of the fluid when averaged out. However, an initial motion can cause a forward motion of the liquid sample at the stop flow junction so that the surface-tension/hydrostatic-pressure balance is overcome locally; the sample fluid meniscus then contacts a capillary region so that flow commences or a drop of liquid forms and falls into the receiving chamber.

Backpressure due to surface tension at the stop flow junction can be reduced by causing a contact to occur between sample at the junction and a movable part. For example, an apparatus can be prepared in which both sample and diluent can be added to the apparatus without starting flow at the restricted flow junction leading to the receiving chamber. A movable part can be included within the apparatus in order to break surface tension at the stop flow junction by contacting the sample at that location. It is possible, for example, to use a lever or any other movable part to restart flow. One embodiment would have a pin (on the tip of the lever) that actually touches the meniscus. Preferred embodiments of the invention using this technique for starting flow contain a mixing bar or similar device in the receiving chamber that is capable of contacting the liquid at the stop flow junction as well as mixing sample and diluent. Numerous magnetically operated stirring bars (not all of which are in the shape of bars, although they are generally referred to by this term because of the common bar shape) are known. These stirring bars typically comprise a magnetic or magnetically susceptible material embedded in a polytetrafluoroethylene or other inert matrix and are actuated by a moving magnetic field that is generated either mechanically (e.g., by rotating or otherwise moving a magnet attached to a motor) or electrically (e.g., by generating a rotating magnetic field, such as that which is used to turn the rotor of an electric motor, or a reciprocating electric current). By using a stirring bar sized closely to fit within the receiving chamber and placing the stop flow junction proximate to the bar location, the normal movement of the stirring bar can be utilized to contact any protrusion of sample meniscus at the stop flow junction. Such protrusions can exist because of hydrostatic pressure transmitted through liquid in the measuring chamber from sample and/or diluent present in the apparatus or because of the geometry of the junction. The bar can be held in place magnetically so that no contact is made during addition of sample to the apparatus. For example, a stirring bar in the shape of a bar can be rotated 90 degrees away from the angle at which contact would normally be made.

In addition to magnetic stirring bars, non-magnetic stirrers of various forms can be used. Mixing with such stirrers is accomplished by mechanical motion, during or after dilution is completed. For example, a sliding plate can be provided which moves back and forth in the receiving chamber when the apparatus is tilted from side to side.

If vibration is used to start flow, a number of variations are possible. For example, a vibrator may be made part of the apparatus. Alternatively, a vibrator may contact the apparatus externally at any location capable of transmitting the vibrational motion to the stop flow junction. This can be at any point of the apparatus if the apparatus is prepared from a rigid material, which is commonly the case. It is also possible to use the motion of the magnetic stir bar to cause vibrations without contact of the stir bar with liquid at the stop flow junction, since rotation of the stir bar will typically cause vibrations within the apparatus. If desired, the vibrations can be increased by including protrusions that the stirring bar strikes in the walls of the receiving chamber or by providing a rough lower surface on which the stirring bar rotates.

Depending on the location and geometry of the stop flow junction and receiving chamber, flow either continues automatically (by capillary action or hydrostatic pressure upon relief of a metastable condition) or additional motions (especially vibrations) or other actions (e.g., contacting the meniscus again) can be utilized to allow a dropwise flow of sample and diluent under the hydrostatic pressure of the diluent until the rising level of liquid in the receiving chamber contacts the region of the stop flow junction, at which time backpressure caused by surface tension is no longer possible and flow continues until the fixed volume receiving chamber is filled. There are no particular restraints on the geometry of the receiving chamber other than that smooth fluid flow be provided for in order to prevent trapping of gas bubbles. Providing entry of sample and diluent into a lower portion of the receiving chamber and providing an upper surface of the receiving chamber that slopes upward toward the vent both aid in avoiding trapped bubbles.

The vent can merely be a small hole terminated by a stop flow junction in order to avoid exit of liquid from the device or can be a more sophisticated vent designed for gas exit without exit of liquid (e.g., a microporous, hydrophobic plug capable of passing air but not hydrophilic liquids).

Although there is no theoretical upper limit on the size of samples that can be measured and diluted using an apparatus of the invention, the method and apparatus are particularly suitable for measuring and diluting small quantities of liquids. Accordingly, the measuring chamber will generally have a volume of from 0.1 $\mu$L to 100 $\mu$L, preferably 1 $\mu$L to 30 $\mu$L, and most preferably 3 $\mu$L to 10 $\mu$L. The receiving chamber generally has a volume of from 3 $\mu$L to 1000 $\mu$L, preferably 10 $\mu$L to 300 $\mu$L, and most preferably 30 $\mu$L to 100 $\mu$L, thereby providing dilution ratios of from $10^4$:1 to 3:1, preferably $10^3$:1 to 10:1, and most preferably 100:1 to 10:1. Channels through which capillary flow will take place will usually have opposing walls spaced in the range of about 0.01 mm to 2 mm, more usually about 0.1 mm to 1 mm. The capillary spaces can be tubular (which does not necessarily intend a circular cross-section but can be square or other regular shapes) or can represent the space formed by flat plates and side walls with the side walls being spaced further apart than a capillary distance. A tubular chamber with at least one flat side (e.g., a square cross-sectional area, a rectangle with adjacent sides differing in length by no more than a factor of 1:2 to 1:4, or a semicircular chamber) are preferred for ease of manufacture in cases where channels are being formed by the joining of two adjacent surfaces, one of which can be flat.

The variability of the sample volume and the diluent volume from device to device and sample to sample will be determined by a number of factors.

1. The geometry of the device, particularly the ratio of length to cross-section of the measuring chamber. In general, the greater the ratio the better the precision. This ratio will determine the extent to which the position of the sample fluid meniscus at flow stop relative to the stop flow junction affects variability.

2. Variation of the dimension of the surface capillary from device to device. State of the art suggests reproducability of about 1%.

3. Variations in the surface tension and contact angle of the surface from sample to sample. There is a limited range of possible values for typical samples of a given type; e.g., plasma. For the preferred dimensions, such variations are not expected to cause significant error.

4. Variability in the extent of displacement of sample by diluent—the factors here are: (a) back flow of sample into the feeder tube; (b) extent of mixing of diluent and sample in the measuring chamber. The variation from sample to sample will be controlled by variations in sample viscosity and density and diluent viscosity and density. The known variability in sample viscosity and density for many typical sample fluids (e.g., plasma) is not very great. It appears that the diluent viscosity and density should ideally not be very much different from that of the sample for best results.

Taking these factors into consideration, estimates of likely variation in sample volume using the preferred dimension range down to less than 1%. Similar considerations apply to the variability of diluent volume except that variation in sample properties become less important (due to dilution).

The time to fill the sample capillary can be calculated from well known physical principles (ref: *Chemical Engineer's Handbook* (1973) 5th Ed., Eds. R. H. Perry & C. H. Chilton, McGraw Hill, New York). In general the time will be minimal. Preferred fill times are less than 5 min; better is less than 1 min; ideally, less than 10 sec. After taking whatever measures are called for to cause the dilution (addition of diluent, activation of any mechanical or electrical device), the time which elapses prior to fluid flow may be significant. Desirable are times less than 1 min, preferably less than 10 sec, most preferably less than 1 sec. The delay in fluid flow apparently results from the creation of an initial metastable condition which is overcome with the passage of time, perhaps by the mechanisms described above in the discussion of an initial metastable flow stop.

The sample application site must be capable of containing sufficient sample to fill the measuring chamber and of allowing sufficiently rapid flow so that sample applied to the sample application site will flow directly to the measuring chamber without being lost by overflowing the sample application site.

The diluent application site must be capable of containing sufficient liquid diluent to fill the measuring chamber through which the diluent flows, any intervening or peripheral flow channels (such as diluent backflowing into the sample application site), and the remainder of the volume inside the receiving chamber not taken up by the sample (or by any movable part or stirring bar present in the receiving chamber). Since flow stops when the receiving chamber is filled with sample and diluent, the dilution ratio is determined by this last volume and the volume of the measuring chamber. For example, if the measuring chamber size is 5 $\mu$l and the receiving chamber has a total interior volume of 120 $\mu$l containing a stirring bar having a volume of 15 $\mu$l, the dilution ratio will be 20:1 (20 volumes of diluent, i.e., 100 $\mu$l, to each unit volume of sample, i.e., 5 $\mu$l).

When using the preferred small volumes in an apparatus of the invention, restricted-flow-junction backpressures in the range of from 0.1 to 20 cm $H_2O$, preferably 0.3 to 10 cm $H_2O$, and most preferably 1 to 5 cm $H_2O$ are used when addition of diluent is intended to automatically restart flow. Backpressures greater than the respective upper limits set forth in the preceding sentence can be used when flow is to be started by some other means.

It should be recognized that statements in this specification indicating upper and lower limits of ranges are to be taken as individually designating a series of upper limits and a series of lower limits which can be utilized in any combination. For example, a typical upper limit and a preferred lower limit may be used in combination to define a range of intermediate preference.

In addition to providing sample dilution and mixing, an apparatus of the invention can also provide automatic incubation of the sample with a first reagent for a specified amount of time prior to mixing and incubating with a second reagent. The incubation times can be made independent of the filling operations. This is accomplished by providing reagents on different surfaces or areas of a surface of the receiving chamber. For example, a first reagent in suitable dry form can be present on the bottom surface of the receiving chamber and a second reagent on the top surface of the chamber. When sample first enters the receiving chamber, it will contact the first reagent. There will then be a tim delay as liquid fills the receiving chamber during which an initial incubation can take place. Mixing can be provided during this time if desired. When the sample and diluent reach the upper surface of the receiving chamber, the second reagent is contacted and enters into the reaction. Any number of zones of reagent can be provided at different places in the receiving chamber. Incubation times can be controlled by varying the height of a band of reagent above the bottom surface of the receiving chamber (for chambers that fill from the bottom up) or otherwise locating the reagent at a point that is reached late in the filling process (e.g., vertical bands at different distances from the stop flow junction when the chamber fills horizontally), by varying the volume and shape of the receiving chamber, and by varying the rate at which diluent enters the reagent chamber.

This last variable can be controlled by providing a "flow restrictor" (which may be part of or different from the stop flow junction). For example controlling the size of the opening between the diluent chamber and the measuring chamber will control flow between them. Additional factors which control the rate at which diluent enters the reagent chamber are the dimensions of the diluent chamber, its height above the stop flow junction, and the cross-sectional area of any point in the flow path through which diluent flows. Also, flow restriction can be achieved at the gas vent from the receiving chamber.

The time to fill the receiving chamber will be controlled by the construction parameters of the device and the viscosity and density of sample and diluent. The ranges of interest are 0.1 sec to 10 min; better is 1 sec to 2 min; best is 10 sec to 1 min. The design parameters described herein, which can be combined with simple experimentation, readily allow selection of a desired fill time.

By providing a diluent chamber much larger than the receiving chamber, variations in flow rates and therefore fill and incubation times will be minimized. However, some variation can still occur if a user does not completely fill the diluent chamber. Accordingly, more accurate control of dilution and incubation times can be achieved by providing a diluent chamber with an overflow chamber for excess diluent and instructing the user to fill the diluent chamber until overflow occurs, thereby providing the same diluent height during each operation of the device. Additional improvements can be achieved by providing a wide cross-sectional area for the diluent chamber so that variation in height from beginning to end of the filling operation is minimized. Such large chambers can be used if desired by filling to a line without providing for an overflow chamber.

Figure 10A:
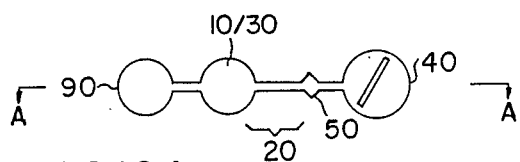
FIGS. 10A and FIG. 10B are horizontal and vertical cross-sections, respectively, showing the internal liquid-contacting surfaces of a tenth embodiment of the invention.
Figure 10B:
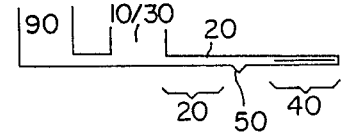
Figure 11:
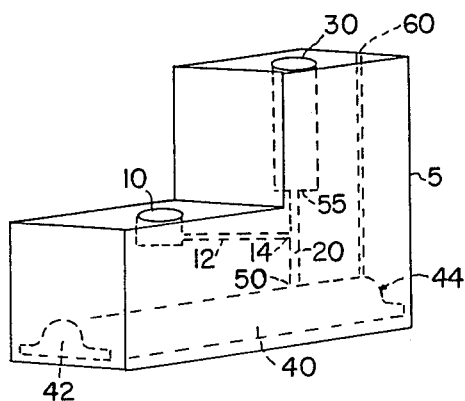
FIG. 11 is a perspective view of an eleventh embodiment of the invention having a vertical sample measuring chamber.
Figure 12:
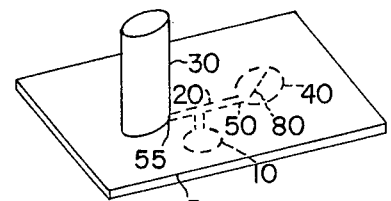
FIG. 12 is a perspective view of a twelfth embodiment of the invention having a horizontal sample measuring chamber.

A series of figures is provided to illustrate a number of embodiments of the invention. The embodiments shown in the figures are not intended to be comprehensive, and numerous other embodiments within the scope of the appended claims will be apparent to those of ordinary skill in the field of the invention. In FIGS. 1-10, only the internal surfaces that contact liquid are shown. FIGS. 11 and 12 show entire apparatuses including both external surfaces (whose edges are marked by solid lines) and internal surfaces (whose edges are marked by dashed lines). Any of the embodiments shown by the internal surfaces of FIGS. 1-10 can be prepared in the form of an actual apparatus resembling FIG. 11, FIG. 12, or a combination or modification of these figures For example, the embodiments shown schematically by means of internal liquid-contact surfaces in FIGS. 1 and 2 closely resemble the embodiment shown in its entirety in FIG. 11. FIGS. 13-15 show embodiments of the invention in multiple views to show both external and internal surfaces.

FIG. 1 is a schematic diagram showing a vertical cross-section of a first embodiment of the invention. Sample application site 10 is a shallow well or depression connected by a thin capillary 12 to measuring chamber 20 at junction 14. Measuring chamber 20 is vertical and has a section 22 above junction 14 and a section 24 below junction 14. When a liquid sample is added to application site 10, liquid flows through capillary 12 and into measuring chamber 20 at junction 14. In FIG. 1 chamber 20 is also of capillary dimensions, by which is meant that the chamber is of sufficiently small cross-sectional area to be filled by capillary action. Capillary action is assisted by gravity in section 24 of chamber 20. When the sample reaches the bottom of chamber 20, flow stops at stop flow junction 50. The portion of chamber 20 above junction 14, identified as section 22 in FIG. 1, is filled by capillary action. Hydrostatic pressure is also available for filling section 28 of chamber 20, but no hydrostatic pressure is available for filling section 26, which is above the fluid level in sample application site 10. In this embodiment of the invention, there is a stop flow junction 55 at the junction of measuring chamber 20 and diluent application site 30, which prevents excess sample from flowing into the diluent application site.

The geometry and surface characteristics of stop flow junction 50 are selected so as to provide sufficient backpressure to overcome the hydrostatic pressure of the sample. This hydrostatic pressure can be calculated from the maximum height of the sample above stop flow junction 50, which (in the embodiment shown in FIG. 1) is the vertical height of the top of the sample application site (10) over stop flow junction 50 (i.e., height 52). The junction is formed by the intersection of the vertical tube that forms chamber 20 with the top horizontal surface of chamber 40. The principal design characteristic controlling backpressure is the cross-section of the junction, the area of which is decreased to provide higher backpressures and increased to produce lower ones.

When diluent is added to diluent application site 30, the resulting increase in hydrostatic pressure overcomes the backpressure at stop flow junction 50 and causes the sample in measuring chamber 20 to be driven by the diluent into receiving chamber 40. Air or any other gas contained in receiving chamber 40 is expelled through vent 60, which is too small to allow exit of fluid (i.e., the vent also acts as a stop flow junction, but one which has a backpressure that the hydrostatic pressure of the diluent is not able to overcome). Numerous other venting arrangements can also be utilized.

In this embodiment of the invention, the means for starting flow at the stop flow junction 50 is merely the additional height of liquid and resulting additional pressure head caused by locating diluent application site 30 higher than measuring chamber 20. Diluent application site 30 is sufficiently large when compared to receiving chamber 40 so that a sufficient pressure head is maintained throughout the dilution operation until receiving chamber 40 is filled (i.e., the pressure head is sufficient to overcome backpressure at stop flow junction 50 even when diluent application site 30 is partially depleted). The pressure head must also be sufficient to overcome any resistance to flow caused by viscous drag in the flow path.

A removable cap 11 (which may be completely removable or hinged or, more preferably, attached to sample application site 10 in a sliding arrangement) can be used to prevent flow of liquid back into the application site. If cover 11 is set in place prior to application of diluent, lack of a vent in this section of the apparatus will resist liquid flow back into the capillary 12. In the absence of a cap, when diluent is added to 30, some initial flow through capillaries 20 and 12 and back into sample application site 10 will occur. When sufficient diluent has been added to 30 so that backpressure at stop flow junction 50 is overcome, flow through measuring chamber 20 into receiving chamber 40 will also occur. A finite time is required to break the surface tension forces at 50, so that flow into receiving chamber 40 lags behind the initial backflow into capillary 12.

The direction and magnitude of fluid flows in the various capillaries and chambers depends on the dimensions of the device, the viscosity and density of the fluids, and the heights of the various liquid columns. After diluent has been added but before flow starts through stop flow junction 50, there will be backflow of sample (and/or diluent) from 20 into 12 and 10. After flow has been initiated through 50, the flow of sample (and/or diluent) from 20 is distributed between 12 and 24 and is controlled by:

A. Pressure head: as pressure increases, flow increases.

B. Tube length: as length increases, flow decreases.

C. Tube cross-section: as cross-section increases, flow increases.

D. Viscosity: as viscosity increases, flow decreases.

The sample will be (a) displaced into receiving chamber 40, (b) displaced into capillary 12, and (c) mixed with diluent in tube 20. The precise disposition of the sample will be controlled by the various factors listed. However, for a given device (and copies made to the same dimensions), specifying these factors ensures that a reproducible quantity of sample will be displaced into receiving chamber 40. It is the reproducibility of sample dilution that is most important in the dilution apparatus, since the actual extent of dilution can readily be adjusted by varying the size of the receiving chamber without significantly affecting the initial measuring of sample and/or types of flow in earlier stages within the device.

Thus (A) by using cap 11 to block backflow through 12, all the flow will be into 40, or (B) by making cross-section 12 much less than cross-section 20, length 24 short in relation to length 12, and pressure head 52 small in relation to pressure head of diluent (70 and 22), backflow into 12 is minimized and can be made negligible relative to flow through 24 into 40.

The precision of the volume of sample displaced into 40 may be compromised by mixing of sample and diluent in tube 20. If the extent of mixing in section 22 of capillary 20 varies from assay to assay, the composition of the fluid moving down section 24 into 40 will also vary. By minimizing the length of section 22, this problem can be made negligible. Other techniques for minimizing mixing have already been discussed.

FIG. 2 shows a similar embodiment, which differs principally in that capillary 12 enters measuring chamber 20 at junction 14 much closer to diluent application site 30. This reduces the hydrostatic pressure at junction 14 and lessens the tendency of diluent and sample to flow backwards through capillary 12 into sample application site 10.

FIG. 3 shows an additional variation of the embodiment shown in FIG. 1. The principal differences are that channel 12 is larger than channel 20 with the effect that measuring chamber 20 begins at junction 14 and extends to restricted flow site 50, which is located well within receiving chamber 40 near the bottom of the chamber. The remainder of the apparatus and its operation are as described above. In this embodiment, adding diluent at site 30 will cause flow through junction 14 and capillary 12 back to sample application site 10. In this embodiment, however, no harm is caused by this reverse flow since the measurement section begins at junction 14 and does not include the connection itself or any part of a tube or other chamber extending from this junction to the diluent application site 30. By not closing off sample application site 10 and by providing channel 12 with a large diameter, backflow is encouraged.

Additionally, by extending tube 20 so that stop flow junction 50 is near the bottom of receiving chamber 40, it is no longer necessary to maintain a large excess of diluent in diluent application site 30. After the surface tension forces at 50 have been overcome and a small volume of sample and diluent has entered receiving chamber 40, the surface of the liquid contacts the bottom of chamber 40 and precludes interruption of flow. Flow of diluent into chamber 40 therefore continues until receiving chamber 40 is filled, even if the hydrostatic pressure head falls below that required to overcome normal backpressure at 50, since the absence of an air gap at stop flow junction 50 prevents backpressure from developing.

The three embodiments discussed above all have capillary chambers as measuring chamber 20. The embodiment shown in FIG. 4 has a measuring chamber 20 that is not capable of filling by capillary action. Stop flow junction 50 is created by having a small exit hole leading from chamber 20 to chamber 40. Since hydrostatic pressure is independent of the volume of fluid, the design of the stop flow junction is no different from those described above. In such embodiments, however, junction 14, the location at which sample enters the chamber, must be located at the top of chamber 20 or sample application site 10 must provide sufficient hydrostatic pressure to fill chamber 20, since capillary action is not available to draw sample upward. The remaining parts of this apparatus and its operation are as described above.

The embodiments above utilize vertical measuring chambers 20. Horizontal (or mixed vertical/horizontal) arrangements are also possible. The embodiment shown in FIG. 5 utilizes a horizontal measuring chamber 20. FIG. 5 also shows a number of other possible variations. For example, a filter 13 is present in sample application site 10. This filter can be, for example, a glass fiber filter capable of separating red blood cells from whole blood, so that a whole blood sample applied at application site 10 is filtered to give a plasma sample withdrawn by capillary 12. Capillary action in chamber 20 is again utilized to fill this chamber. Stop flow junction 50 prevents flow of sample into receiving chamber 40. A second stop flow junction 55 prevents sample from entering diluent site 30. By locating the diluent application site vertically above stop flow junction 50, hydrostatic pressure is again available to drive sample into receiving chamber 40. This embodiment also contains a stirring bar 80 or other means for mixing the sample and diluent in chamber 40.

By slightly rearranging the geometry of the embodiment shown in FIG. 5, it is possible to use mixing bar 80 as the means for starting flow. By locating the stop flow junction 50 at the bottom of chamber, as shown in FIG. 6, the sample meniscus at 50 can be contacted by stirring bar 80 when it rotates, thereby allowing rotation of the stir bar to actuate flow. Since a high pressure head is not required, diluent application site 30 can be located at a lower height, insufficient to overcome backpressure at stop flow junction 50. However, diluent site 30 must provide sufficient hydrostatic pressure to fill chamber 40 once flow starts.

A variation on the geometry of the embodiment shown in FIG. 6 is set forth in FIG. 7, which shows a plan view from above rather than a vertical cross-section. Sample application site 10 is connected to a capillary measuring chamber 20 by connection 12. Junction 14 can be located at any point along measuring chamber 20. The cross-sectional area of tube 12 is much smaller than that of tube 20. Diluent application site 30 is located at one end of chamber 20 (connected by stop flow junction 55), while receiving chamber 40 is located at the other end (connected by stop flow junction 50). A stir bar 80 is located in receiving chamber 40, which is vented (not shown). Diluent application site 30 is located above or contains walls which extend sufficiently above the height of receiving chamber 40 to allow diluent to drive sample into the receiving chamber. However, the height difference is not sufficient to overcome the backpressure at stop flow junction 50. Rather, this backpressure is relieved when the sample meniscus at 50 is contacted by stirring bar/means for starting flow 80.

It is also possible to operate this apparatus, or any of the apparatuses described above, by using vibration as the means for starting flow. Motion of the fluid at the stop flow junction is sufficient to overcome backpressure if the amplitude and frequency of the vibration are sufficient. Only a slight hydrostatic pressure is then required to maintain flow, or flow can be maintained by using a capillary receiving chamber, as discussed below.

Figure 8:
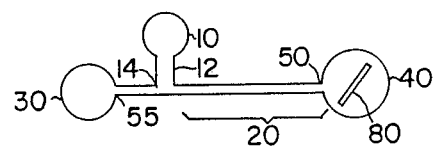
FIG. 8 is a horizontal cross-section showing the internal liquid-contacting surfaces of an eighth embodiment of the invention

FIG. 8 shows a variation of the embodiment shown in FIG. 7, in which back flow through junction 14 to sample application site 10 is permitted. The cross-sectional area of tube 20 is much narrower than that of tube 12. Measuring chamber 20 therefore is measured from junction 14 to stop flow junction 50, as was described above for FIG. 3. The remaining parts an operation of this apparatus are as described in FIG. 7.

Figure 9:
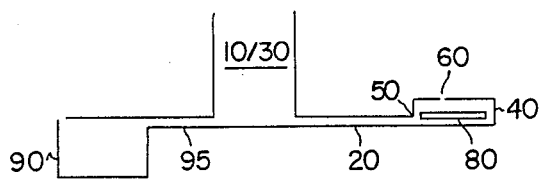
FIG. 9 is a vertical cross-section showing the internal liquid-contacting surfaces of a ninth embodiment of the invention.

FIG. 9 shows an embodiment of the invention in which a single application site serves both for application of sample and application of diluent. The cross-sectional view shown in FIG. 8 has an application site 10/30 to which sample is initially added. The capillary channel 20 serves as the measuring chamber. A sump 90 is utilized to draw off excess sample through connection 95. A vent (62) is provided in sump 90. An absorbant material, such as cotton, can be present in sump 90 to absorb liquids, if desired. By providing sump 90, excess sample is withdrawn so that essentially no sample remains in application site 10/30 when diluent is later added. The small quantity of sample which remains in 10/30 can be made negligible compared to the sample volume (20) by appropriate choice of dimensions. Sufficient excess diluent is added to cause the sample held in measuring chamber 20 to be driven into receiving chamber 40. By sizing sump 90 so that it is sufficient to retain excess sample but insufficient to contain the amount of diluent added to application site 10/30, the apparatus can be operated with the certainty of driving sample into the receiving chamber. The remaining parts of the apparatus and their use are as described above.

Embodiments of the invention can be designed so as to rely solely upon capillary action to move fluids between parts. FIGS. 10A and 10B represent horizontal and vertical cross-sectional views of such an apparatus. The principal difference between this and the previous embodiment of FIG. 9 is that receiving chamber 40 is capable of filling by capillary action. Stop flow junction 50 is a small but abrupt widening in a capillary tube By utilizing capillary spaces throughout, extremely small volumes can be measured and mixed. Sample applied at site 10/30 will fill chamber 20, but will not initially flow past stop flow junction 50. Diluent may be added to application site 10/30 without causing flow if the hydrostatic pressure remains sufficiently low. However, once vibration or a sharp motion causes the sample to cross the gap at site 50, flow continues by capillary action into receiving chamber 40. A separate vibrator may be provided or chamber 40 may be provided with a rough bottom surface or other indentations that make contact with stir bar 80 when in operation in order to use this stir bar to vibrate the apparatus sufficiently to cause flow to start.

FIG. 11 is a perspective view showing an apparatus of the invention (including exterior surfaces shown by dashed lines) in which the measuring chamber 20 is vertical and the means for starting flow is the difference in vertical height between diluent application site 30 and stop flow junction 50. Receiving chamber 40 traverses the length of the block in which the various chambers are formed so as to provide two end windows, 42 and 44, which define an optical path for measurement. Vent 60 is shown as passing upward through block 5 to an exit at a height equivalent to the upper portion of diluent application site 30. Placing the actual vent exit at this height and maintaining a small internal vent volume by maintaining a small vent diameter minimize error caused by entry of liquid into the vent. Since the vent exit is above the height of diluent remaining in diluent application site 30 after receiving chamber 40 has filled, hydrostatic pressure is not available to cause leakage out of the vent. The apparatus of FIG. 11 can be prepared from two or more separate pieces having internal chambers or surface depressions that form the indicated internal cavities when the pieces are placed together.

FIG. 12 shows a perspective view of an embodiment of the invention in which measuring chamber 20 is horizontal, in a manner similar shown in FIGS. 5 and 6 (vertical cross-sectional views) and 7 and 8 (plan views). In this embodiment, all parts except for diluent application site 30 can be prepared in the form of a two-piece, thin, plastic card-like device of the type described in U.S. patent application Ser. No. 880,793, filed July 1, 1986. The diluent application site 30 is prepared by attaching an upward-extending cylinder to the surface of the flat device at the appropriate location. In the embodiment shown, stir bar 80 acts as the means for starting flow in a manner similar to that described for the embodiment shown in FIG. 6. However, it is also possible to start flow utilizing hydrostatic pressure from diluent in application site 30 in a manner similar to that shown in FIG. 5. The other parts of the apparatus and their operation have been discussed previously.

FIGS. 13-15 are described in detail in the examples which follow.

FIG. 16A shows a perspective view of a junction that is not intended to stop flow at a junction between two chambers but is rather intended to encourage flow past that intersection. A capillary-sized groove 15 is provided to encourage flow from capillary 12 into chamber 20. Sample flows from channel 12 into groove 15. As shown in the vertical cross-sectional view of FIG. 16B, junction 14 between capillary 12 and chamber 20 would otherwise act as a stop flow junction. By providing capillary groove 15, sample is encouraged to creep past junction 14. Groove 15 is of capillary dimensions and is capable of capturing sample from channel 12 and drawing it past junction 14. Groove 15 does not necessarily extend completely around chamber 20 as shown in FIG. 16 but need only provide a capillary connection between the intersecting chambers.

All of the apparatuses of the invention whether or not discussed above can be used in a common method, although there are some variations in means for carrying out individual steps. A sample is added to a sample application site of an apparatus in all cases. Sample flows without the application of external energy (i.e., no pump, vacuum, air pressure, or the like is utilized) from the sample application site into a fixed volume measuring chamber. The fixed volume measuring chamber is terminated by one or more stop flow junction which stops sample flow prior to addition of diluent. Diluent is then added to a diluent application site of the same apparatus. The two steps of adding sample and adding diluent are usually carried out in the order stated since both the diluent application site and the sample application site are connected to the measuring chamber. If diluent is added first, diluent rather than sample would be measured in the measuring chamber. However, certain embodiments can have diluent present in the apparatus before sample is added if provision is made for exclusion of the diluent from the measuring chamber until sample is present in the measuring chamber. For example, a collapsible diluent bag can be placed in the diluent application site prior to addition of sample. After sample is added to the device and fills the measuring chamber, the bag is ruptured. A barrier of rupturable impermeable material can also be used to prevent diluent from entering the measuring chamber prematurely. Simultaneous addition of sample and diluent coupled with different flow rates into the measuring chamber (sample flow being faster than diluent flow) can also achieve the same result. The essential characteristic is that the sample chamber fills with sample prior to filling with diluent. Whether this is achieved by mechanical valves, rupturable seals, order of sample and diluent application, or any other means, is immaterial to the practice of the invention.

The diluent added is capable of flowing through the measuring chamber and stop flow junction and into a fixed volume measuring chamber. However, this flow does not necessarily occur without external activation to start flow. In some instances, no external activation is required, since the additional hydrostatic pressure caused by adding diluent to the diluent application site can be sufficient to overcome the backpressure due to surface tension at the stop flow junction. In other cases, the hydrostatic pressure is insufficient, and some other means of starting flow must be used, as described above.

During the filling of the receiving chamber, air or any other fluid trapped therein is released through a vent. The vent is either sufficiently small to form a stop flow junction so that liquid is trapped in the receiving chamber or the vent exit is located at a level higher than that of diluent in the diluent application site so that hydrostatic pressure cannot force significant volume of liquid out of the receiving chamber.

The apparatuses of the invention are quite simple, both in construction and operation compared to other automatic measuring devices. Typically, no moving valves or other parts are present other than (in some embodiments) a stirring bar or a movable part for contacting the liquid surface at the stop flow junction in order to reinitiate flow. This part may be magnetically movable and can further be utilized as the stirring bar to mix the diluent and the sample in the receiving chamber.

The stop flow junction of the present invention can be readily designed using the criteria set forth herein and known physical principles relating backpressure and liquid flow to changes in chamber diameters, surface tensions of liquids, pressure heads, and the like. Some exemplary calculations are set forth in the following examples.

The invention now being generally described, the following examples are presented for purposes of illustration only. These examples are not intended to be limiting of the invention but can be used to define preferred embodiments.

EXAMPLE 1

An automatic measuring and diluting device was designed and built to exemplify the present invention. This device quantitatively measures a first fluid and automatically adds a specified amount of diluent upon the addition of diluent to a reservoir. The apparatus is shown in FIG. 13. The device comprises a solid acrylic block 5 (into which various chambers are formed by drilling and other plastic-cutting operations) along with a flat plate 6 used to form the bottom of the device. A plan view of the device is shown in FIG. 13A with lines B—B and C—C showing the locations of the sectional views shown in FIGS. 13B and 13C. In plan view 13A, the openings of sample chamber 10 and diluent chamber 30 are seen in the top faces of two portions of the block. Measuring chamber 20 is seen at the bottom of chamber 30. Vent 60 is seen on a lower portion of the block, as will be more clearly seen in sectional views.

FIG. 13B shows a sectional view in which all internal chambers and channels except for the vent are visible. A capillary channel 12 connects sample chamber 10 to measuring chamber 20, which it enters at junction 14. Since capillary 12 is smaller in diameter than chamber 20, junction 14 is provided with an outward taper as channel 12 enters chamber 20 in order to prevent generation of backpressure due to surface tension forces at this junction. Chamber 20 is a vertical tube having a stop flow junction 50 at the junction of measurement chamber 20 and receiving chamber 40. A stop flow junction 55 is also present at the top of chamber 20 where it connects with diluent chamber 30. Receiving chamber 40 has a lower section 45 that is slightly wider than the upper portion of chamber 40 in order to hold in place a flat rectangular plate (not shown) that is used to mix the fluids in chamber 40. Lower block 6 forms the lower surface of chamber 40 below portion 45. Lower plate 6 is connected to block 5 by screws (not shown).

FIG. 13C shows a cross-sectional view through the device at right angles to the view shown in FIG. 13B. Vent 60 is seen exiting a lower horizontal surface of block 5 at the opposite end of chamber 40 from stop flow junction 50. The flat plate (not shown) used to mix the liquids in chamber 40 occupies a small portion of the slot shown as section 45 in the lower portion of chamber 40 and mixes fluid by sliding from side to side in the device as shown in FIG. 13C. Also visible in FIG. 13C is a small section in the roof of receiving chamber 40 at stop flow junction 50 that extends lower into the chamber than the remainder of the roof. This feature is important in preventing liquid from contacting reagent on the upper roof of chamber 40 during the initial stages of filling chamber 40 and also ensures that gas in chamber 40 is displaced by sample and diluent without being trapped as a bubble.

Stop flow junction 50 of the device shown in FIG. 13 is the junction of a vertical tube with a horizontal plane that forms an upper surface of chamber 40. The actual dimensions of the interior chambers shown in the embodiment of FIG. 13 are set forth in the table below.

TABLE 1

| Chamber/Tube Number | Radius mm | Length mm | Volume μl | Description |
| --- | --- | --- | --- | --- |
| 10 | 2.35 | 10.77 | 187.0 | Sample Appl. Site |
| 12 | 0.17 | 7.95 | 0.72 | Connecting Channel |
| 20 | 0.52 | 5.87 | 3.1 | Measuring Chamber |
| 30 | 5.00 | 26.21 | 2060.0 | Diluent Chamber |
| 40 | — | 10.00 | 55.0 | Receiving Chamber |

An estimate of the maximum height of the diluent surface over junction 50 was made using the Young-Laplace equation. Assuming $R = 0.0515$ cm (the radius of the capillary tube 20), $\gamma = 60$ dynes/cm (a reasonable value for human blood plasma), and $\rho$ (the diluent density) $= 1.00$ g/cc, a value of 2.4 cm $H_2O$ was obtained. In practice a somewhat different value will be found because of surface defects in the device and contact angle effects.

An equation describing the time to fill capillary tubes 12 and 20 has been developed. The effects of gravity were not allowed for: such effects are not expected to have a major effect in the device of FIG. 13.

Time to fill the connecting channel and sample capillary. Sample fluid is applied to application site 10 from which it flows by capillarity into connecting channel 12 and measuring chamber 20. The time to fill these channels is given by:

$$t = \frac{2\pi\mu}{\gamma\cos\theta}\left[\frac{(L_{12})^2}{R_{12}} + \frac{2L_{20}(L_{12})(R_{20})^3}{(R_{12})^4} + \frac{(L_{20})^2}{R_{20}}\right]$$

where:
R=radius (as in Table 1)
L=length (as in Table 1)
$\mu$=viscosity: 0.010 g/cm sec
$\gamma$=surface tension: 60 dynes/cm
$\theta$=contact angle: 40 degrees
12=connecting channel
20=measuring chamber The calculated fill time was equivalent to the experimentally measured fill time within the expected experimental margin of error.

Receiving chamber 40 is shaped to provide several operating characteristics. It contains a stir bar in lower section 45 that remains flat on the bottom surface of the chamber in order to avoid interfering with the passage of light through the principal long dimension of the chamber. This chamber section has a pathlength of 1 cm and flat ends for light to enter and exit, thereby providing a generally useful cuvette segment. The stir bar is made of teflon containing metal particles in order to allow reciprocal motion under the influence of a reciprocating magnetic field. This motion results in mixing of liquids in the chamber.

Two or more reagents can be present in receiving chamber 40. The first reagent can be applied to the surface of chamber 40 near stop flow junction 50 or to the stirrer bar and is contacted by sample and diluent immediately upon the entry of these fluids into chamber 40. A second reagent is applied to the upper horizontal surface of chamber 40 a the left end of the chamber (as viewed in FIG. 13C) and is not contacted by liquid until fluid filling the chamber reaches this area. Accordingly, sequential mixing of reagents with fluid entering the reaction and analysis chamber can be accomplished with a controlled time span to allow incubation of the first reagent with the sample prior to contact with the second reagent.

Incubation time is provided by controlling the rate of flow of diluent into the receiving chamber. Flow control can be provided by preparing a restriction in the upper neck of measuring chamber 20 or by providing means in chamber 30 for controlling diluent flow. For example, in the embodiment shown in FIG. 13, a washer-like device containing a small central hole was placed into firm contact with the bottom perimeter surface of chamber 30. The rate of fluid flow from chamber 30 is then controlled by the diameter of the hole in the washer. The washer or other flow control device has no other effect on the operation of the device since the flow control at junction 50 depends only on fluid height. For example, the amount of time required to fill the receiving chamber for a cartridge with dimensions given in Table 1 without a flow restrictor is about 0.1 second. With a flow restrictor of radius 0.08 mm and length 7.5 mm, the fill time is 65 seconds (using parameter values given previously).

The time to fill the mixing chamber depends on the dimensions of the diluent chamber, measuring chamber and receiving chamber, as well as the viscosity and density of the liquid. The time to fill is given by:

$$t = \frac{8\mu (R_{30})^2}{\rho g}\left\{\frac{V_{40}}{\pi (R_{30})^6} + \left[L_{20}\left(\frac{1}{(R_{20})^4} - \frac{1}{(R_{30})^4}\right) + L_r\left(\frac{1}{(R_r)^4} - \frac{1}{(R_{30})^4}\right)\right] \times \ln\left[\frac{L_{30} + L_{20} + L_r}{L_{30} + L_{20} + L_r - \frac{V_{40}}{\pi(R_{30})^2}}\right]\right\}$$

where
g=gravitational acceleration
$\mu$=fluid viscosity
p=fluid density
R=radius
V=volume
L=length
30=diluent chamber
20=measuring chamber
40=receiving chamber
r=flow restrictor The calculated and actual fill times for the receiving chamber were in agreement within experimental error.

Initial observations of the test device have proven its ability to measure, dilute, and mix small volumes of liquids in the desired user-friendly manner for which the device was designed. Experiments used aqueous solutions of dye and human blood plasma as samples and buffered saline solution (100 mM sodium phosphate pH 7, containing 0.13M NaCl) as diluent. Prior to use the device was subjected to plasma etching to reduce the contact angle with aqueous solutions. The observed contact angle varied from 30°-70° depending on etching and previous use of the device. When added to the sample application site all the above fluids filled the connecting channel and the measuring channel. Flow stopped in all cases at junctions 55 and 50. When diluent was gradually added to a depth of greater than 2 cm in the diluent chamber, sample was rapidly displaced from the measuring chamber above 14 and from the connecting channel 12 back into sample site 10. Flow subsequently (within a few seconds) occurred from the part of measuring channel below 14 into 40. As judged by removal of dye, all the sample in tube 20 below 14 was displaced into 40. Chamber 40 filled without any air being trapped, and flow stopped when vent 60 had filled. Chamber 40 filled from right to left as shown in FIG. 13C, rather than from bottom to top.

EXAMPLE 2

An additional embodiment of the type generally shown previously in FIG. 9 was also constructed to demonstrate operation of the invention. The device was constructed from plastic strips 0.65 mm thick which were plasma etched to promote fluid flow. The strips were cut to appropriate sizes, and holes were drilled to serve as various chambers, vents, and application sites. The strips were stuck together with double-stick tape 0.09 mm thick having track designs excised so that capillary tracks were formed between the various cartridge components. Assembly of the plastic strips and double-stick tape to form an actual device is shown in FIG. 14. FIG. 14A is a plan view while FIG. 14B is a sectional view along line D—D shown in FIG. 14A. Sample/diluent application site 10/30 was created by drilling a 4.0 mm diameter hole through top plastic strip 5 and middle plastic strip 7. No holes were drilled in bottom plastic strip 9. Chamber 20 was formed by a track design excised from lower double-stick tape 8. The track had a width of 1.0 mm. A similar track 95 joined application site 20/30 to sump 90 which contained stacked filter paper 100 to absorb excess sample. Receiving chamber 40 was formed by drilling a 4.0 mm diameter hole in plastic strip 7 A 0.5 mm diameter hole in plastic strip 5 above chamber 40 provided vent 60. A small steel stir bar 2.5 mm in length (80) was provided in chamber 40. Capillary tracks 20 and 95 were 10 and 5 mm in length, respectively.

One drop of blood was applied to the application site and flowed down both tracks. Flow down track 20 terminated at stop flow junction 50, which was much deeper and wider than the track. All the remaining blood moved down track 95 until application site 10/30 was empty, the blood being absorbed into filter paper 100 in sump 90. In this way, a defined sample volume was isolated in measuring chamber 20. Excess diluent (isotonic saline) was then added to application site 10/30, and stir bar 80 was turned using an external rotating magnetic field (provided by a laboratory stirrer). Contact of stir bar 80 with the leading edge of the blood sample broke the liquid surface and caused flow to resume, flow being driven by gravity. The blood in measuring chamber 20 was completely displaced by diluent, and flow continued until receiving (mixing) chamber 40 was filled with blood and diluent.

EXAMPLE 3

A third embodiment similar to that shown in FIGS. 7 and 8 was prepared for diluting plasma after plasma was passed through a filter as described in U.S. application Ser. No. 924,633, filed Oct. 29, 1986. This device is shown in FIG. 15 in which FIG. 15A is a plan view and FIG. 15B is a cross-sectional view taken along line E—E of FIG. 15A.

The device was prepared from plastic strips and double-stick tape as described for the embodiment of Example 2. The diameters of the various drilled chambers and vents were as follows: sample application site 10, 4.0 mm; diluent application site 30, 4.0 mm; receiving (mixing) chamber 40, 4.0 mm; and vent 60, 0.5 mm. Measuring chamber 20 had a length of 2.5 cm and a width of 1.0 mm. Introductory sample channel 12 had a length of 4.0 mm, a width of 1.0 mm, and was located at the extreme left end of track 20 as shown in FIG. 15A. A glass fiber filter 0.65 mm thick (Tojo GA200) was present in sample application site 10. Stir bar 80 was identical to that used in the embodiment of Example 2.

One drop of blood was applied to the filter in sample application site 10. Plasma free of red cells emerged into track 12 and flowed into measuring chamber 20 until the measuring chamber was completely filled. Flow stopped at stop flow junctions 50 and 55. Diluent (water) was added to diluent application site 30. Flow did not start until stir bar 80 was rotated. Once flow began, the diluent displaced all the plasma from measuring chamber 20 into receiving (mixing) chamber 40. Flow continued until chamber 40 was full.

To visualize the plasma, dye was added to a blood sample prior to an experiment. There was no significant backflow of sample into track 12 (presumably because the filter provided significant resistance to flow).

All publications and patent applications mentioned in this specification are indicative of the level of skill of those skilled in the art to which this invention pertains. All United States patents and applications are herein incorporated by reference to the same extent as if each individual patent or application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An apparatus for automatically diluting an aqueous sample with an aqueous diluent, comprising:
    housing means containing
        sample application site means for receiving a sample;
        measuring chamber means having a first volume;
        receiving chamber means having a second volume, wherein said second volume is greater than said first volume;
        diluent application site means for receiving a diluent;
        first flow means for delivering a sample from said sample application site means to said measuring chamber means by the sum of capillary and gravitational forces upon addition of sample to said sample application site means;
        second flow means for delivering diluent from said diluent application site means to said measuring chamber means by the sum of capillary and gravitational forces upon addition of diluent to said diluent application sit means;
        third flow means for delivering sample and diluent from said measuring chamber means to said receiving chamber means by the sum of capillary and gravitational forces; and
        a stop flow junction located in said third flow means and adapted to the surface tension characteristics of the sample so as to provide sufficient back pressure resulting from contact between said sample and wall means of said housing means at said stop flow means to prevent sample from flowing through said stop flow junction in absence of diluent but allowing flow through said stop flow junction when diluent is present in said apparatus along with said sample,
    whereby addition of diluent to said diluent application site means after sample is added to said sample application site means causes hydrostatic pressure at said stop flow junction to exceed said backpressure, whereby said diluent expels sample from said measuring chamber means and causes a fixed ratio of sample to diluent to be delivered to said receiving chamber means.

2. The apparatus of claim 1, wherein said stop flow junction comprises an increase in flow path cross-section from a capillary-flow region to a non-capillary-flow region.

3. The apparatus of claim 1, wherein said stop flow junction comprises a change in liquid contact surfaces.

4. The apparatus in claim 1, wherein said stop flow junction produces a backpressure of from 0.1 to 20 cm $H_2O$ when sample is present at said junction.

5. The apparatus of claim 1, wherein said measuring chamber means has a volume of from 0.1 $\mu L$ to 100 $\mu L$.

6. The apparatus of claim 1, wherein said receiving chamber means has a volume of from 3 $\mu L$ to 1000 $\mu L$.

7. The apparatus of claim 1, wherein said measuring chamber means has a volume of from 1 $\mu L$ to 30 $\mu L$ and said receiving chamber means has a volume of from 10 $\mu L$ to 300 $\mu L$, with the proviso that the receiving chamber means is larger than the measuring means chamber.

8. The apparatus of claim 1, wherein the diluent application site means has a minimum volume equal to the volume of the receiving chamber means and a maximum volume of 10 mL.

9. The apparatus of claim 1, wherein the backpressure at the stop flow junction is from 0.1 to 10 cm $H_2O$ and the vertical height difference in cm between the minimum diluent height and the stop flow junction is greater than the numerical value in cm $H_2O$ of said backpressure.

10. The apparatus of claim 1, further comprising a removable, air-tight cover for said sample application site means.

11. The apparatus of claim 1, wherein said measuring chamber means is a capillary chamber.

12. The apparatus of claim 1, wherein said stop flow junction is located at the bottom of said receiving chamber means.

13. The apparatus of claim 1, wherein capillarity is present in said receiving chamber means.

14. The apparatus of claim 19, wherein capillarity is present throughout all internal chambers of said apparatus except at said stop flow junction.

15. The apparatus of claim 1, wherein a first reagent is present at a first location in said receiving chamber means and a second reagent is present at a second location in said receiving chamber means different from said first location.

16. The apparatus of claim 1, wherein said diluent application site comprises an internal chamber in said housing means and said internal chamber contains diluent, said diluent being prevented from entering said measuring chamber means by a barrier of rupturable impermeable material.

17. A method for diluting an aqueous sample with an aqueous diluent, comprising:
adding an unmeasured volume of said sample to sample application site means of a device in which said sample flows by the sum of capillary and gravitational forces to measuring chamber means having a first volume, said measuring chamber means being terminated by a stop flow junction which stops sample flow as a result of backpressure resulting from interaction of said sample with wall means of said device at said stop flow junction; and then
adding said diluent to diluent application site means of said device, wherein said diluent flows by the sum of capillary and gravitational forces to said measuring chamber means and displaces sample into receiving chamber means having a second volume larger than said first volume when hydrostatic pressure resulting from the presence of diluent in said device exceeds said backpressure, whereby a fixed ratio sample and diluent fills said receiving chamber means.

18. The method of claim 17, further comprising sealing said sample application site means after sample has filled said measuring chamber means.

19. The method of claim 17, further comprising contacting said sample and said diluent with a first reagent at a first location in said receiving chamber means prior to contacting a second reagent at a second location in said receiving chamber.

20. The method of claim 19, wherein said sample and diluent are incubated for a specific time with said first reagent prior to contacting said second reagent, said time being determined by the rate of filling of said receiving chamber means, said rate being controlled by a flow restrictor that controls the flow of diluent from said diluent application site means.

21. The method of claim 17, wherein said stop flow junction comprises an increase in flow path cross section from a capillary-flow region to a non-capillary-flow region.

22. The method of claim 17, wherein said stop flow junction comprises a change in liquid contact surfaces.

23. The method of claim 17, wherein said stop flow junction produces a back pressure of from 0.1 to 20 cm $H_2O$.

24. The method of claim 17, wherein said measuring chamber means has a volume of from 0.1 $\mu L$ to 100 $\mu L$.

25. The method of claim 17, wherein said receiving chamber means has a volume of from 3 $\mu L$ to 1,000 $\mu L$.

26. The method of claim 17, wherein said diluent application site means has a minimum volume equal to the volume of the receiving chamber means and a maximum volume of 10 mL.

27. The method of claim 17, wherein said measuring chamber means is a capillary chamber.

* * * * *